United States Patent
Koh et al.

(10) Patent No.: US 7,310,551 B1
(45) Date of Patent: Dec. 18, 2007

(54) DIAGNOSTIC GAUGE FOR CARDIAC HEALTH ANALYSIS

(75) Inventors: Steve Koh, South Pasadena, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 210 days.

(21) Appl. No.: 11/144,425

(22) Filed: Jun. 2, 2005

(51) Int. Cl.
*A61B 5/044* (2006.01)

(52) U.S. Cl. ............. 600/523; 600/509; 600/512; 600/513; 607/18

(58) Field of Classification Search .......... 600/481, 600/508, 509, 510, 513, 515–519, 523, 525; 607/2, 6, 9, 18, 27, 30, 32, 59, 60
See application file for complete search history.

(56) References Cited

U.S. PATENT DOCUMENTS

| | | | | |
|---|---|---|---|---|
| 4,592,364 | A * | 6/1986 | Pinto ............. | 600/485 |
| 5,713,938 | A * | 2/1998 | Chiang et al. ........ | 607/32 |
| 5,803,084 | A * | 9/1998 | Olson ............. | 600/512 |
| 6,301,503 | B1 * | 10/2001 | Hsu et al. .......... | 607/30 |
| 6,438,410 | B2 * | 8/2002 | Hsu et al. .......... | 600/516 |
| 6,572,557 | B2 * | 6/2003 | Tchou et al. ........ | 600/483 |
| 6,599,250 | B2 | 7/2003 | Webb et al. ........ | 600/483 |
| 2002/0161295 | A1 * | 10/2002 | Edwards et al. ....... | 600/420 |
| 2003/0083582 | A1 * | 5/2003 | Hirsh ............. | 600/509 |
| 2003/0093125 | A1 * | 5/2003 | Zhu et al. .......... | 607/25 |
| 2003/0195397 | A1 | 10/2003 | Bardy ............ | 600/300 |
| 2004/0059238 | A1 | 3/2004 | Fischell et al. ...... | 600/515 |
| 2004/0122296 | A1 | 6/2004 | Hatlestad et al. ..... | 600/300 |
| 2006/0089679 | A1 | 4/2006 | Zhu et al. | |
| 2006/0253044 | A1 * | 11/2006 | Zhang et al. ........ | 600/512 |

FOREIGN PATENT DOCUMENTS

EP     1400259 A1     3/2004

\* cited by examiner

*Primary Examiner*—Kristen D. Mullen
*Assistant Examiner*—Eugene T Wu

(57) ABSTRACT

A diagnostic gauge for cardiac health is described. Multiple parameters pertaining to a patent's cardiac health are distilled to a single diagnostic vector having an angle and a magnitude. The diagnostic vector is plotted on a Cartesian graph to form a visual gauge that provides a general assessment of the patient's cardiac health given the underlying parameters. This allows care providers to diagnose more quickly a patient's cardiac health through observation of the gauge without having to review all of the measured parameters. Additionally, the diagnostic gauge can be used to screen for those patient's with conditions that require more immediate attention. A trend of the diagnostic vectors can also be developed and plotted to reveal changes in the patient's cardiac health over time.

19 Claims, 9 Drawing Sheets

DIAGNOSTIC GAUGE FOR CARDIAC HEALTH ANALYSIS

TECHNICAL FIELD

The present invention generally relates to implantable devices and systems for analyzing parameters related to a patient's health. More particularly, this invention relates to techniques for simplifying parameter analysis when screening patients for possible heart failure.

BACKGROUND

Heart failure is a condition in which the heart is unable to pump enough blood to sustain normal bodily functions. Heart failure may affect either the right side, left side, or both sides of the heart. As pumping action is lost, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

Implantable cardiac devices, such as pacemakers and defibrillators, monitor many different parameters that may be used to determine how well a patient's heart is functioning. For instance, implantable cardiac devices can measure morphology-related parameters, impedance, intrinsic heart rate, heart rate recovery, heart rate variability, conduction delay, pressure, posture, activity, and so forth. Each of these parameters can be used evaluating the patient's heart.

The implantable cardiac devices are commonly configured to stimulate the heart with electrical pulses in response to individual or combinations of these measured parameters. Additionally, the devices can store these parameters over time and occasionally transmit the parameters to external diagnostic systems for more exhaustive analysis. The frequency of offloading data from the device is directed by a clinician or physician.

Certain parameters may be used as surrogate data for diagnosing potential heart failure. Changes in the parameters over time may suggest improvement or degradation in a patient's cardiac condition. However, it is difficult to ascertain from cursory examination of raw parameters whether the patient's condition is improving or worsening. Additionally, in some treatment environments, a clinic may routinely collect data from many patients. With increasing time demands on physicians, clinicians, and other care providers and the large amount of data parameters being collected from numerous patients, it is difficult to diagnose whether individual patients exhibit improving or deteriorating cardiac health based merely on a cursory review of the many raw parameters collected by the implantable devices.

Accordingly, there is a need to simplify parameter analysis in a way that assists care providers in quickly diagnosing the cardiac health of one or more patients. This would allow care providers to screen for patients exhibiting certain patterns that might warrant closer scrutiny, and would be particularly helpful for identifying those patients whose conditions have degenerated to a point of requiring immediate attention.

SUMMARY

Techniques for diagnosing a patient's cardiac health by analyzing parameters and presenting results in an easy-to-understand graphical diagnostic gauge are described. The multiple parameters are distilled to a single diagnostic vector having an angle and a magnitude. The diagnostic vector is plotted on a Cartesian graph to form a visual gauge that provides a general assessment of the patient's cardiac health given the underlying parameters. This allows care providers to diagnose more quickly a patient's cardiac health through observation of the gauge without having to review all of the measured parameters. Additionally, the diagnostic gauge can be used to screen for those patient's with conditions that require more immediate attention.

In one implementation, an implantable medical device measures multiple parameters indicative of a patient's cardiac health. The parameters are classified depending upon whether increases in their values are deemed an improvement or a degradation of cardiac health. Once classified, the parameters are converted to vectors that align with diagonals of the Cartesian graph defined by linear equations $y=x$ (for parameters where increase is better) and $y=-x$ (for parameters where decrease is better). The diagnostic vector is computed from the individual parameter vectors and plotted on the Cartesian graph.

The Cartesian graph defines multiple zones, where individual zones have associated diagnostic interpretations of a patient's cardiac health. The zones may also be color coded to convey visual cues as to the degrees of wellness. The angle of the diagnostic vector places it in one of the zones to identify the diagnostic interpretation of the patient's cardiac health. The vector's magnitude can be interpreted as an indication of significance, providing a measure of agreement among the multiple parameters.

In another implementation, multiple diagnostic vectors are computed from sets of parameters measured over time and stored. A trend of the diagnostic vectors is developed to evaluate whether the patient's health is improving or deteriorating. Based on this trend, a care provider can prescribe therapies to improve the patient's health.

DETAILED DESCRIPTION

Overview

The following discussion describes techniques for diagnosing a patient's health by analyzing multiple parameters and presenting the results in an easy-to-understand graphical presentation. The parameters may be measured using an implantable medical device, such as implantable cardiac devices (e.g., pacemakers, defibrillators), implantable neurological devices, and other implantable devices that sense data related to human health. The parameters may also be measured via an external device with implanted or subcutaneous sensors. The parameters are processed and analyzed to interpret the patient's health. The processing and analysis can be implemented within the implantable device (assuming it is configured with sufficient memory and processing capabilities) or alternatively at an external device, such as a programmer or diagnostic computing system.

For discussion purposes, the techniques are described in the context of diagnosing heart conditions and the potential of heart failure. Within this context, the implantable medical device is configured as an implantable cardiac device that measures parameters that can be used as surrogates for diagnosing heart failure (e.g., intrinsic heart rate, conduction delay, activity, evoked response amplitude, etc.). The parameters are processed to produce data points, which over time might be suggestive or predictive of heart failure. For some parameters, an increase over time is a good result showing improvement in the patient's health. For others, a decrease over time is considered good.

The techniques described below consider all of the parameters to determine whether the patient is generally getting better or worse. The parameters are distilled and presented in a graphical "diagnostic gauge" that allows a care provider to ascertain at-a-glance whether the patient's condition is improving or deteriorating.

This disclosure describes first an exemplary implantable cardiac device. This device can be characterized as a miniature computing device that is implanted into the body of a patient to monitor, regulate, and/or correct heart activity. Such devices include implantable cardiac stimulation devices (e.g., implantable cardiac pacemakers, implantable defibrillators, cardiac rhythm management devices) that apply stimulation therapy to the heart and implantable cardiac monitors that monitor and record heart activity for diagnostic purposes. Following explanation of the implantable device is a description of a diagnostic system and techniques for assimilating the numerous parameters into the graphical gauge.

Implantable Cardiac System

Figure 1:
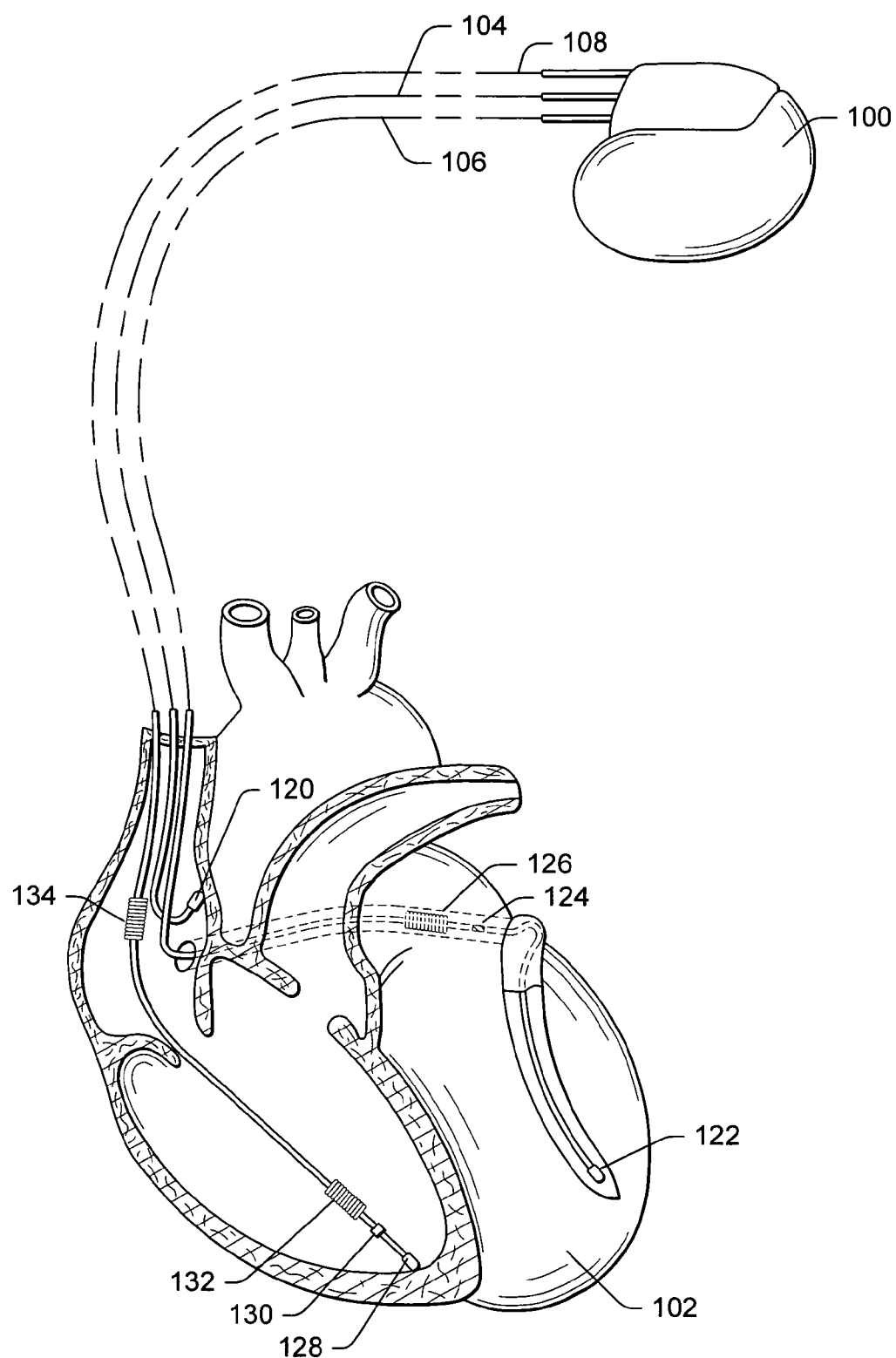
FIG. 1 is a diagrammatic illustration of an implantable cardiac device in electrical communication with a patient's heart for multi-chamber sensing and delivery of multi-chamber stimulation and shock therapy.

FIG. 1 shows an exemplary implantable cardiac device 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
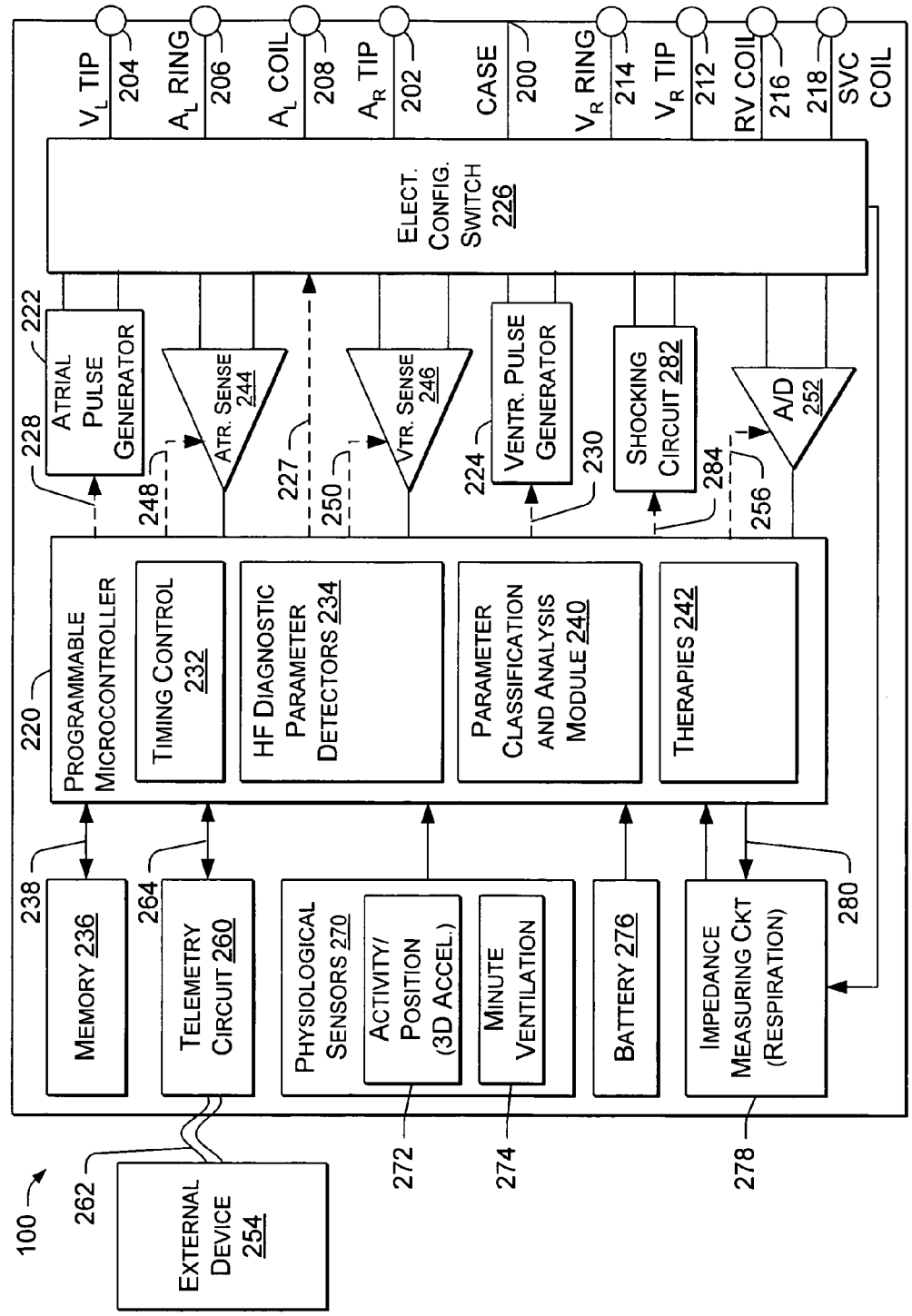
FIG. 2 is a functional block diagram of the multi-chamber implantable cardiac device.

FIG. 2 shows an exemplary, simplified block diagram depicting various components of the implantable cardiac device 100. The components are housed in housing 200, which is often referred to as the "can", "case", "encasing", or "case electrode". Housing 200 may be programmably selected as a return electrode for unipolar modes or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

- a right atrial tip terminal (AR TIP) 202 for atrial tip electrode 120;
- a left ventricular tip terminal (VL TIP) 204 for left ventricular tip electrode 122;
- a left atrial ring terminal (AL RING) 206 for left atrial ring electrode 124;
- a left atrial shocking terminal (AL COIL) 208 for left atrial coil electrode 126;
- a right ventricular tip terminal (VR TIP) 212 for right ventricular tip electrode 128;
- a right ventricular ring terminal (VR RING) 214 for right ventricular ring electrode 130;
- a right ventricular shocking terminal (RV COIL) 216 for RV coil electrode 132; and
- an SVC shocking terminal (SVC COIL) 218 for SVC coil electrode 134.

The implantable cardiac device 100 includes a programmable microcontroller 220 that controls various operations, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches. To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A-A) delay, or ventricular interconduction (V-V) delay, etc.). The timing control circuitry may also be used for the timing of refractory periods, blanking intervals, noise detection windows, evoked response windows, alert intervals, marker channel timing, and so on.

Microcontroller 220 is also equipped with multiple detectors 234 used to detect or compute parameters indicative, suggestive, or predictive of heart failure (HF). Examples of HF parameter detectors 234 include an arrhythmia detector to detect arrhythmia parameters, a morphology detector to detect morphological parameters, impedance circuitry to detect DC impedance (e.g., transthoracic impedance), activity sensor to detect activity and activity duration, posture sensors to sense posture or patient position, exercise compliance monitor to evaluate exercise compliance, heart rate detectors to detect heart rate and heart rate variability, pressure sensors to detect pressure, cardiac output sensors, and so forth. It is noted that these detectors are examples and others types of detectors may be employed. Essentially, the microcontroller 220 may implement any detector that produces a parameter that may be used alone or in combination with another to predict or diagnose heart failure.

The HF parameters are stored in memory 236, which is coupled to the microcontroller 220 via a suitable data/address bus 238. In addition to these parameters, the memory 236 stores programmable operating parameters used by the microcontroller 220 to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

Microcontroller 220 also implements a parameter classification and analysis module 240 that processes the multiple HF diagnostic parameters collected by the HF parameter detectors 234 to derive a diagnostic vector indicative of the patient's cardiac health. The parameter classification and analysis module 240 classifies the parameters received from the HF parameter detectors 234 according to a binary rule of either (1) increase equals better or (2) decrease equals better. In the first instance, an increasing value of the parameter means that the patient is getting better. Examples include activity duration, evoked response amplitude, activity, and heart rate variation. In the second instance, a decreasing value means the patient is getting better. Examples include heart rate and conduction delay. It is noted that the binary rule can be restated in the converse as (1) decrease equals worse or (2) increase equals worse.

Once the parameters are classified, the module 240 derives the diagnostic vector from the numerous parameters. The diagnostic vector is plotted on a two-dimensional Cartesian graph according to the vector's magnitude and angle. The magnitude measures a degree of agreement among the parameters. If the parameters agree, the magnitude will be larger. The angle places the vector in different regions or zones of the Cartesian graph. Each zone has an associated interpretation of whether the patient is currently healthy or not. Additionally, if the vector is located in a zone associated with a poor condition, an alert is generated to inform the clinician of the poor condition and that the patient might need more immediate care.

In this manner, the parameter classification and analysis module 240 effectively decreases the number of data points to be interpreted by physicians or clinicians when attempting to diagnose heart failure. The numerous parameters are assimilated into a single vector that can be used as an assessment of the patient's cardiac health, and the likelihood that the patient is heading toward heart failure.

The diagnostic vectors can be computed for different sets of HF parameters collected over time and stored in memory 236. This provides a series of diagnostic vectors computed over time. As individual parameters change over time, the diagnostic vector will move about the diagnostic graph, often times transitioning from one zone to another. Changes in the diagnostic vector provide insight as to whether the patient's health is improving or deteriorating over time. Trend analysis may be applied to the vectors, with the results presented in another graphical manner that informs the care provider of the patient's improving or worsening condition. Furthermore, if the diagnostic vector is trending to a worsening condition, an alert may be generated to inform the clinician of the worsening condition.

The microcontroller 220 may further be programmed to prescribe one or more pacing therapies 242 in response to results from the module 240. For example, if the module 240 predicts that conditions are worsening and heart failure may be imminent, the microcontroller 220 may prescribe a pacing therapy that attempts to counteract the parameters suggesting a worsening condition.

The components 234, 240, and 242 may be implemented in hardware as part of the microcontroller 220, or as software/firmware instructions programmed into the device and executed on the microcontroller 220 during certain modes of operation. These components may further be implemented independent from the microcontroller 220. Although not shown, the microcontroller 220 may further include other dedicated circuitry and/or firmware/software components that assist in monitoring various conditions of the patient's heart and managing pacing therapies.

The implantable cardiac device 100 has atrial sensing circuits 244 and ventricular sensing circuits 246 to detect the presence of cardiac activity in each of the four chambers of the heart. The sensing circuits 244 and 246 may be selectively coupled to the right atrial lead 104, coronary sinus lead 106, and the right ventricular lead 108 through the switch 226. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity. Each sensing circuit 244 and 246 may employ one or more low power, precision amplifiers with programmable gain and/or automatic gain control, band pass filtering, and threshold detection circuitry to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

The implantable cardiac device 100 is further equipped with an analog-to-digital (A/D) data acquisition system 252 to sample cardiac signals across any pair of desired electrodes. The system 252 is coupled to the right atrial lead 104, the coronary sinus lead 106, and the right ventricular lead 108 through the switch 226. Cardiac signals received from the leads are supplied to the data acquisition system 252, which is configured to acquire intracardiac electrogram (IEGM) signals, convert the raw analog data into a digital signal, and store the digital signals for processing.

The data acquisition system 252 is coupled to the microcontroller 220, or other detection circuitry, to assist in detecting various parameters and events. For instance, the system 252 acquires the signals used by the HF parameter detectors 234 to detect parameters indicative of suggestive of heart failure. The data acquisition system 252 is further configured to detect an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The data acquired by the data acquisition system 252 is stored in memory 236 and can be subsequently transmitted to an external device 254. The external device 254 may be implemented in many ways, including as a programmer, a transtelephonic transceiver, or a diagnostic system analyzer. Additionally, the external device 254 may be representative of an intermediate communication device that receives information from the implantable device and relays the information to another device or system for evaluation. In this manner, the HF diagnostic parameters and/or the results from the parameter classification and analysis module 240 may be output to the external device 254 for further analysis or presentation to the clinician.

In one implementation, a telemetry circuit 260 facilitates communication between the implantable device 100 and the external device 254. During programming or data output, the telemetry circuit 260 establishes a communication link 262 with the external device 254. In addition to downloading data to the external device, operating parameters for the implantable device 100 may be non-invasively programmed into the memory 236 by transmission from the external device 254 over link 262 and through the telemetry circuit 260. The microcontroller 220 activates the telemetry circuit 260 with a control signal 264. The telemetry circuit 260 allows intracardiac electrograms and status information relating to the operation of the device 100 (as contained in the microcontroller 220 or memory 236) to be sent to the external device 254 through an established communication link 262.

The implantable device 100 may include magnet detection circuitry (not shown), coupled to the microcontroller 220, to detect when a magnet is placed over the device 100. A magnet may be used by a clinician to perform various test functions of the device 100 and/or to signal the microcontroller 220 that the external programmer 254 is in place to receive or transmit data to the microcontroller 220 through the telemetry circuit 260.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor(s) 270 may further be used to detect changes in cardiac output, changes in the physiological condition of the heart, diurnal changes in activity (e.g., detecting sleep and wake states), or respiration activity (e.g., minute ventilation). The microcontroller 220 responds to changes sensed by the sensor(s) 270 by adjusting various pacing parameters (such as rate, AV Delay, V-V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient. Examples of physiologic sensors that may be implemented in device 100 include sensors that, for example, sense respiration activities, $O_2$ saturation, evoked response, pH of blood, and so forth.

In the illustrated implementation, the physiological sensors 270 include sensors for detecting patient activity and respiration. Any sensor capable of sensing such conditions, either directly or indirectly, may be used. In particular, the physiological sensors 270 include an activity sensor 272 to detect patient movement. The activity sensor 272 may be implemented in many ways, including as a three-dimensional (3D) DC accelerometer. In one configuration, the accelerometer output signal is bandpass-filtered, rectified, and integrated at regular timed intervals. The processed accelerometer signal is used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting state. The activity variance can be monitored diurnally to detect the low variance in the measurement corresponding to the sleep state.

An exemplary physiological sensor used to detect respiratory conditions is a minute ventilation (MV) sensor 274. The MV sensor 274 senses minute ventilation, which is the total volume of air that moves into and out of a patient's lungs in a minute. The MV sensor 274 uses transthoracic impedance, which is a measure of impedance across the chest cavity, to sense air movement. Lungs filled with air have higher impedance than empty lungs. Thus, upon inhalation, impedance increases and upon exhalation, impedance decreases. Other respiration sensors that may be used in addition to, or instead of, the MV sensor 274 include an $O_2$ sensor that measures oxygen-related parameters, a sensor to measure respiration rate, and a sensor to measure tidal volume. The activity and respiratory signals generated by the sensors 270 are passed to the microcontroller 220 for measurement by the HF parameter detectors 234.

The implantable cardiac device 100 additionally includes a battery 276 to supply operating power to various components shown in FIG. 2. The battery 276 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that elective replacement time can be detected. As one example, the device 100 employs lithium/silver vanadium oxide batteries.

The implantable cardiac device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring thoracic impedance for many uses including determining shock thresholds; detecting when the device has been implanted; measuring stroke volume; and detecting the opening of heart valves; and so forth. The impedance measuring circuit 278 can be used to measure respiration-related parameters, such as respiration rate, minute ventilation, respiration signal amplitude, and tidal volume. The impedance measuring circuit 278 is coupled to the switch 226 so that any desired electrodes may be used.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 Joules), moderate (e.g., 0.5-10 Joules), or high energy (e.g., 11 to 40 Joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV coil electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Diagnostic System

In the above described implementation, parameter classification and analysis is implemented within the implantable cardiac device 100. In other implementations, parameter classification and analysis may be partially or fully implemented in computing devices external to the implantable device 100. For instance, the parameter classification and analysis may be implemented in an external programmer or in diagnostic computers used by the physician to analyze parameters suggestive of heart failure. One such system implementation is described below.

Figure 3:
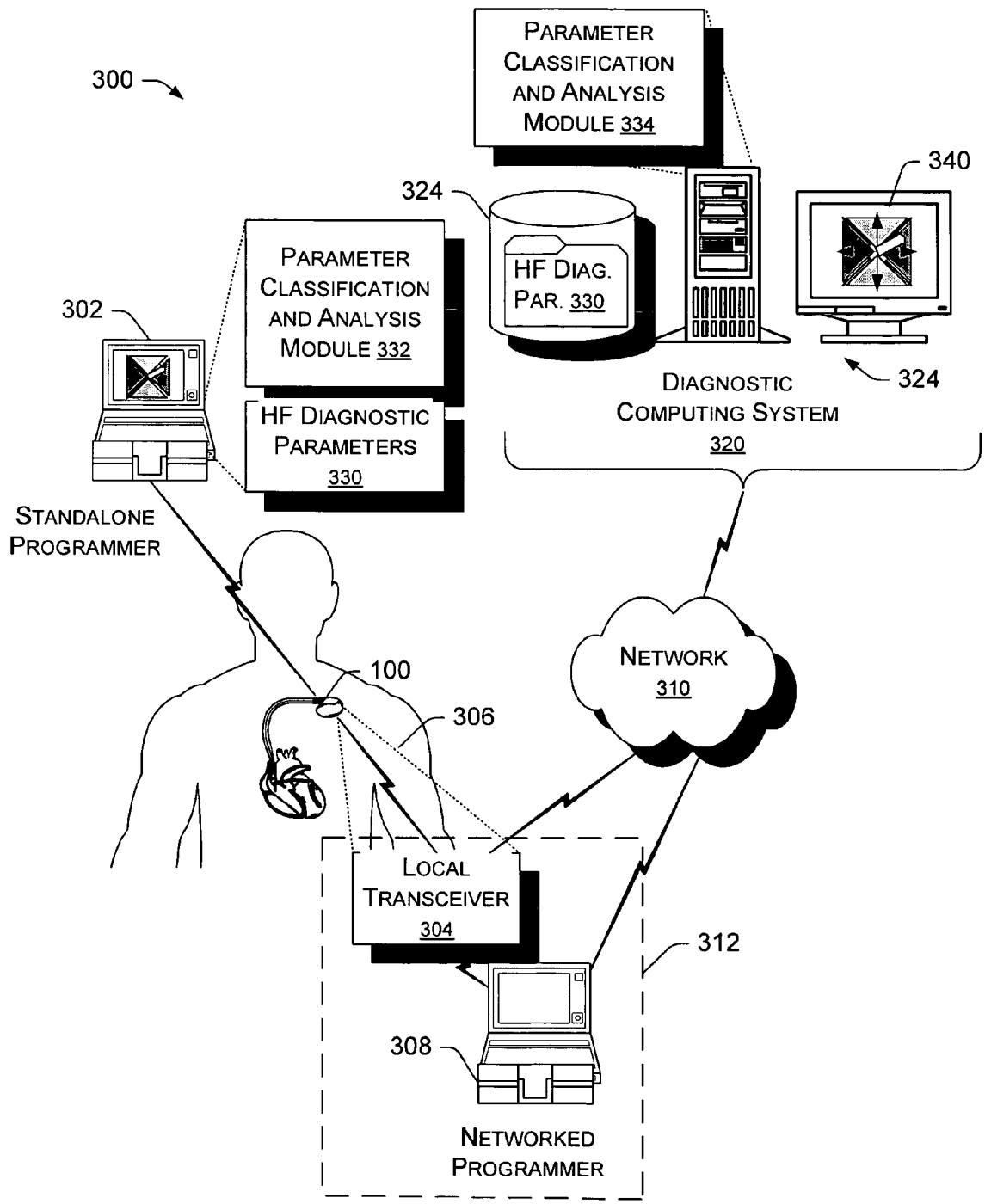
FIG. 3 is a diagrammatic illustration of a diagnostic system where the implantable cardiac device transmits data to one or more external devices for further processing.

FIG. 3 shows a HF diagnostic system 300 that includes the implantable cardiac device 100 in communication with one or more external devices that are capable of conducting diagnostics on data parameters received from the implantable device. The implantable device 100 measures and stores parameters over time. Depending upon the size of the memory, the device may store parameters collected over many days or months. The parameters are then occasionally transmitted from the device 100 to one or more external devices. The data may be downloaded, for example, during physician checkups or other specified times. The external devices are configured with more processing and memory capabilities than the implantable device, and hence are able to conduct a more exhaustive analysis of the parameters.

The external devices may be implemented as a programmer, a computer, and/or a network of computing systems and data storages units. In this illustration, the implantable device 100 communicates with a standalone or offline programmer 302 via short-range telemetry technology. The offline programmer 302 is equipped with a wand that, when positioned proximal to the device 100, communicates with the device 100 through an electromagnetic coupling.

The implantable cardiac device 100 can alternatively, or additionally, be configured to communicate with a local transceiver 304 that is proximally located near the patient. The local transceiver 304 may be configured as an electronic communication device that is worn by the patient or is situated on a structure within the room or residence of the patient. The local transceiver 304 communicates with the implantable device 100 using short-range telemetry or longer-range high-frequency-based telemetry, such as RF (radio frequency) transmissions. Alternatively, the local transceiver 304 may be incorporated into the implantable device 100, as represented by dashed line 306. In this case, the device includes a separate and isolated package area that accommodates high-frequency transmissions without disrupting operation of the monitoring and stimulation circuitry.

The local transceiver 304 communicates with other external computing devices directly or via a network. In the illustrated implementation, the transceiver 304 transmits parameters received from the implantable device 100 to a networked programmer 308, which is connected to a network 310. The networked programmer 308 is similar in operation to standalone programmer 302, but differs in that it has a network port for connection to the network 310. The networked programmer 310 may be local to, or remote from, the local transceiver 304 depending upon the implementation and transmission range. Alternatively, the local transceiver 304 may be incorporated into the networked programmer 308, as represented by dashed line 312. Another possible implementation is for the local transceiver 304 to be connected directly to the network 310 for communication with remote computing devices and/or programmers including, for example, diagnostic computing system 320. Diagnostic computing system 320 includes one or more computers 322 for processing data received from the device 100 and a data store 324 for storing the device data.

The network 310 may be implemented by one or more different types of networks (e.g., Internet, local area network, wide area network, telephone, cable, satellite, etc.), including wire-based technologies (e.g., telephone line, cable, fiber optics, etc.) and/or wireless technologies (e.g., RF, cellular, microwave, IR, wireless personal area network, etc.). The network 310 can be configured to support any number of different protocols, including HTTP (HyperText Transport Protocol), TCP/IP (Transmission Control Protocol/Internet Protocol), WAP (Wireless Application Protocol), Bluetooth, and so on.

The HF diagnostic parameters detected by the device 100 and offloaded to the external devices for further analysis are stored at the external devices. In FIG. 3, the HF diagnostic parameters 330 are shown stored in programmer 302 and the data store 324 of computing system 320.

The external devise are equipped with logic to process the parameters received from the device 100, as well as any other parameters that might warrant consideration when diagnosing a patient's health (e.g., a patient's weight, age, etc.). In this example, the standalone programmer 302 implements a parameter classification and analysis module 332 to analyze the HF diagnostic parameters 330 that are stored locally, and the diagnostic computer 322 implements a parameter classification and analysis module 334 to analyze the HF diagnostic parameters 330 stored in data store 324.

The parameter classification and analysis module classifies the HF diagnostic parameters into one of two categories: (1) increase equals better (or decrease equals worse) or (2) decrease equals better (or increase equals worse). Thus, parameters in which an increasing value is generally understood to be an improving health condition are classified in the first category, while parameters in which a decreasing value is generally understood to be an improving health condition are classified in the second category. The measured parameters can be normalized based on medically accepted standard value and weighted based on patient's diagnosis. Once normalized, the parameters in the first category are converted into first vectors, where each first vector has an angle that aligns with a diagonal of a Cartesian graph defined by the linear equation y=x. The parameters in the second category are converted into second vectors, where each second vector has an angle that aligns with a diagonal of the Cartesian graph defined by the linear equation y=−x. Application of these functions forms vector coordinates (x, y) for each parameter.

It is noted that in other implementations, the vectors may be arranged in ways other than along diagonals. More generally, the parameters can be converted into first vectors having an angle on the Cartesian graph defined by the linear equation $y=x*\tan(\theta)$ and second vectors having an angle on the Cartesian graph defined by the linear equation $y=-x*\tan(\theta)$.

The parameter vectors are summed to produce a diagnostic vector representative of the diagnostic parameters. The diagnostic vector has a magnitude and an angle. The vector can be plotted on a two-dimensional Cartesian graph according to the magnitude and angle. The graph defines diagnostic zones that are associated with simplified diagnoses of a patient's cardiac health. The graph may be pictorially presented and color coded to convey visual cues as to degrees of wellness. The diagnostic vector is plotted on the graph to form an easy-to-understand diagnostic gauge that gives the care provider a quick understanding of the patient's general cardiac health.

One example screen 340 with the diagnostic gauge is shown depicted on diagnostic computer 322. In this example, the diagnostic gauge includes a single vector plotted on the two-dimensional graph. This gauge is shown in more detail below with respect to FIG. 4. The screen 340 may further include raw statistical values of the parameters, as well as a language narrative or declarative statement (e.g., "Based on the HF diagnostic parameters X, Y, and Z, the patient's cardiac health is improving").

The analysis performed by the module 332 or 334 does not involve complex computation, and hence may be implemented on computing devices of limited computational power, such as a handheld PDA.

Diagnostic Gauge

Figure 4:
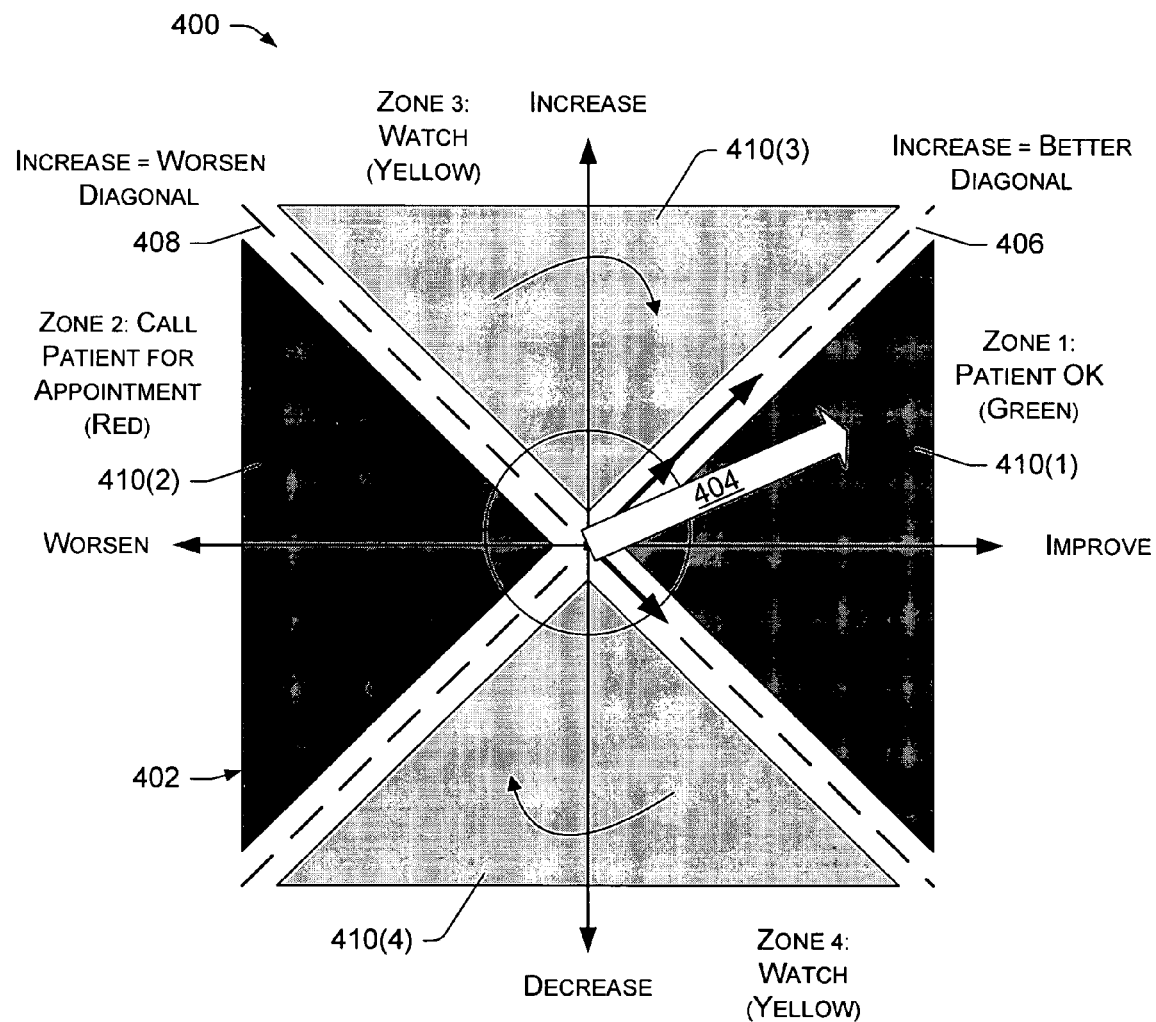
FIG. 4 illustrates one exemplary graphical representation of a diagnostic gauge used in analysis of a patient's cardiac health.

FIG. 4 shows the diagnostic gauge 400 that may be depicted on screen 340 in more detail. The gauge 400 consists of a two-dimensional Cartesian graph 402 and a diagnostic vector 404 plotted thereon. The vector 404 extends outward from the origin (0, 0) to resemble a needle of an instrument gauge. In this manner, the gauge 400 forms a user-friendly cardiac "speedometer", reducing a number of heart-related parameters to a single reading that quickly informs the care provider of the general condition of the patient.

The graph 402 depicts two diagonal lines 406 and 408 as dashed lines. The first diagonal 406 extends at 45° and 225° according to the function y=x. The second diagonal 408 extends at 135° and 315° according to the function y=−x. The two diagonals 406 and 408 define four zones 410(1), 410(2), 410(3), and 410(4). Each zone has an associated diagnostic meaning. The first zone 410(1), between 45° and 315° and spanning the positive x-axis, means that the patient exhibits satisfactory or good health. The second zone 410(2), between 135° and 225° and spanning the negative x-axis, means that the patient exhibits poor health conditions and should be examined as soon as possible. The third and fourth zones 410(3) and 410(4), between 45° and 135° along the positive y-axis and between 225° and 315° along the negative y-axis, mean that the patient's condition should be scrutinized more closely as the patient is either improving or worsening.

In other implementations, the zones vectors may be oriented or sized differently than that shown in FIG. 4. For instance, the zones may be defined by other intersecting lines that follow a more general linear equation of $y=\pm x*\tan(\theta)$.

When presented on a display, the zones of the diagnostic graph may be color coded to aid the care provider with visual cues. For instance, zone 1 may be colored green to imply a satisfactory condition, whereas zone 2 may be colored red to imply a warning, alerting the care provider to take action. Zones 3 and 4 can be colored yellow, suggesting that closer scrutiny is warranted as a precaution.

Parameters classified in the "increase equals better" category are plotted as vectors along the first diagonal 406, as represented by two superimposed vectors at 45°. Conversely, parameters classified in the "decrease equals better" category are plotted as vectors along the second diagonal 408, as represented by the single illustrated vector at 315°.

The parameter-based vectors are summed to produce the single diagnostic vector 404. The resulting angle of vector 404 places the vector in one of the four zones, thereby establishing the patient's general prognosis. The vector's magnitude measures a degree of agreement among the multiple parameters. If the parameters agree, the magnitude will be larger. The magnitude may be compared to a minimum threshold that is graphically illustrated as a circle about the origin in FIG. 4. This threshold can be set by the care provider. If the diagnostic vector does not exceed the threshold, the corresponding set of parameters have values that are too dispersed and when summed, do not produce a vector of sufficient significance to give confidence to an interpretation.

With the gauge 400, a care provider can discern at-a-glance whether the patient is generally of satisfactory health (i.e., the vector extends into green zone 1), or poor health (i.e., the vector is in red zone 2), or is somewhere between (i.e., the vector resides in one of the yellow zones 3 or 4). As the patient is examined over time and her health condition changes, the vector 404 will spin about the graph 402 and change in magnitude according to changes in the underlying parameters measured by the implantable cardiac device. When the vector projects into the red zone 2, the diagnostic system 300 may generate alarms in the form of warning statements, visual cues, audible sounds, and the like, to inform the care providers to take suitable action. A red zone reading may be interpreted, for example, as impending heart failure.

Parameter Classification and Analysis

One exemplary implementation of parameter classification and analysis will now be described in this section. For discussion purposes, only a few parameters are used for inputs. However, in practice, any number of parameters may be used. The classification and analysis may be implemented, for example, by the parameter classification and analysis module implemented at the implantable device 100 or an external device (e.g., programmer 302 and/or computer 322).

Initially, the parameters detected by the implantable device 100 are classified according to how changes in the parameters affect a patient's health. For some parameters, an increase in value is perceived as a good result or an improving condition. One such example parameter is activity duration. When activity duration increases above a predetermined baseline, this is generally recognized as a good result. Other examples in this category include evoked response amplitude, activity, and heart rate variation.

For other parameters, a decrease in value is thought to be a positive outcome or an improving condition. One example in this second category is conduction delay. It is generally perceived as a good result if the measured conduction delay is less than a baseline value. Another example in this category is heart rate, as a decreasing heart rate is generally positive.

The measured parameters are compared against predetermined baseline values and different linear functions applied depending upon the classification category. In one implementation, a delta is computed between the parameter's current value and its corresponding baseline value (i.e., Δ=current value−baseline). In the Cartesian graph 402, y is equal to the delta (i.e., y=Δ=current value−baseline). Once the delta is computed, the appropriate linear function is applied. A linear function y=x is applied to parameters classified in the "increase equals better" (or "decrease equals worse") category and a linear function y=−x is applied to parameters classified in the "decrease equals better" (or "increase equals worse") category. Application of these functions to respective parameters forms vector coordinates (x, y) for each parameter. The vector coordinates orient the parameter vectors along diagonals in a Cartesian graph. Vectors for parameters in the first category have angles that align with the diagonal of the Cartesian graph defined by y=x, whereas vectors for parameters in the second category have angles that align with the diagonal of the Cartesian graph defined by y=−x.

As an example, consider the activity parameter which is classified in the first or "increase equals better" category. Suppose the device measures activity at a value of 40 and the normal baseline for activity is 30. The delta for this situation is +10 (i.e., Δ=40−30=10). Since the activity parameter is classified in the "increase equals better" category, the linear function y=x is applied, where y=Δ=10 (y=x=+10), to form vector coordinates of (+10, +10). When plotted on the Cartesian graph, the parameter vector runs along the 45° diagonal.

As another example, consider the conduction delay parameter which is classified in the second or "decrease equals better" category. Conduction delay is the delay sensed in the contraction difference between the left ventricle and the right ventricle. Longer durations are considered worse than shorter durations. Suppose the device measures a conduction delay of 100 ms, but the normal baseline is 70 ms. The delta for this case is 30 ms (i.e., Δ=100−70=30). Since the conduction delay is classified in the "decrease equals better" category, the linear function y=−x is applied, where y=Δ=30 (y=−x, so x=−30) to form vector coordinates of (−30, +30). When plotted on the Cartesian graph, the vector runs along the 135° diagonal.

Figure 5:
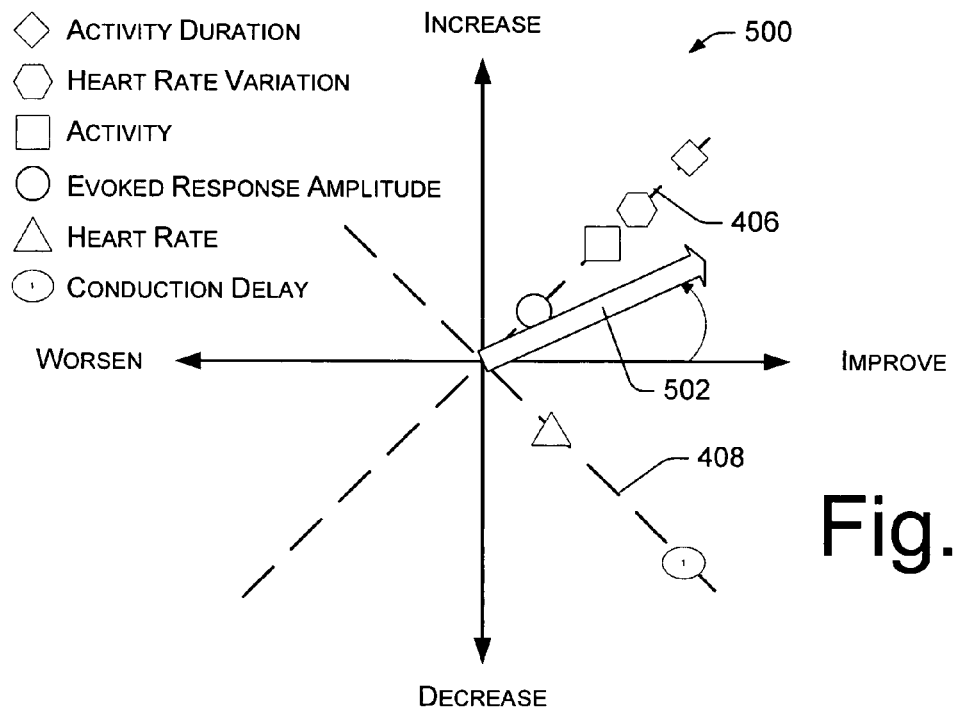
FIGS. 5-7 show parameters plotted on a Cartesian graph to demonstrate how a diagnostic vector of the diagnostic gauge (FIG. 4) is computed based on those parameters.
Figure 6:
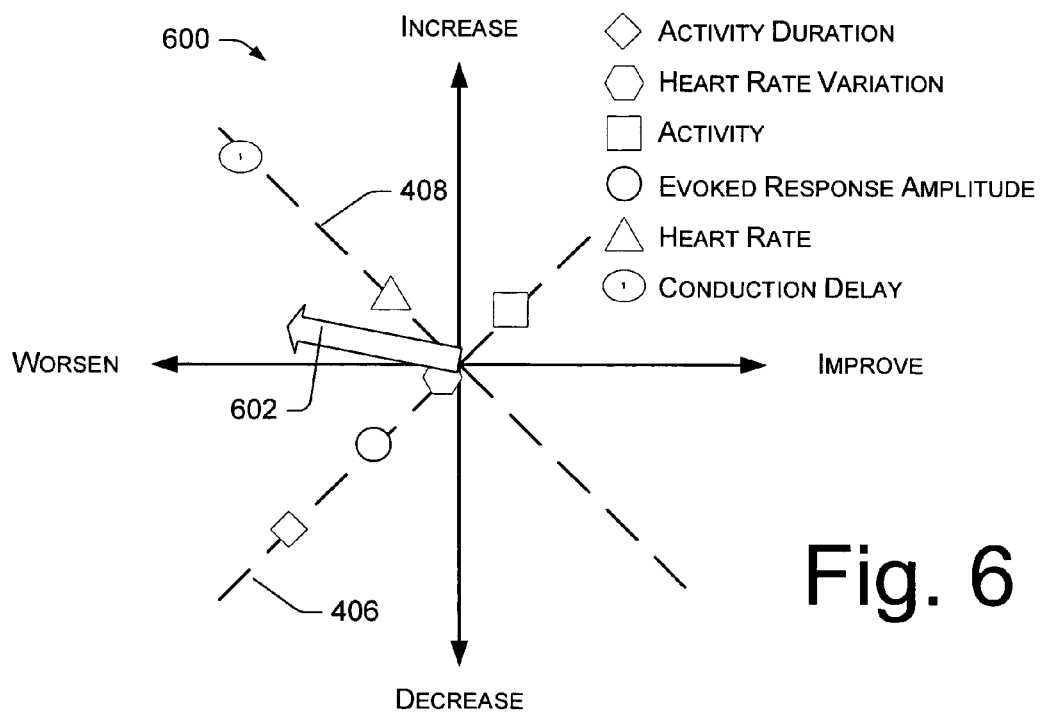

FIGS. 5 and 6 show two exemplary Cartesian graphs 500 and 600, respectively, with six parameters plotted thereon. Four parameters in the "increase equals better" category (i.e., activity duration, evoked response amplitude, activity, and heart rate variation) are plotted along the first diagonal 406. Two parameters in the "decrease equals better" category (i.e., heart rate and conduction delay) are plotted along the second diagonal 408. The vectors of individual parameters have angles along the diagonals and magnitudes represented by the individually shaped endpoints (e.g., the vector tip of activity duration is represented by a diamond, the vector tip of activity is represented by a square, and so forth). In FIG. 5, the vectors for parameters in the "increase equals better" category all have 45° angles, while the vectors for parameters in the "decrease equals better" category all have 315° (or −45°) angles. By contrast, in FIG. 6, some of the vectors in the first category have 225° angles and both vectors in the second category have 135° angles.

The diagnostic vector 404 is computed by summing the six vectors using vector algebra. Notice that vectors within the same category have the same angle and differ only in magnitude. Thus, a composite vector for each category can be computed by simple addition of the magnitudes. Said another way, composite category vectors can be formed by addition of all X values and addition of all Y values.

For vectors $(X_i, Y_i)$ for $i=1$ to $N$,

Category Vector$(X_C, Y_C) = (X_1 + X_2 + \ldots + X_N, Y_1 + Y_2 + \ldots + Y_N)$ This yields two composite category vectors A and B, where vector A is defined by coordinates $(X_{C1}, Y_{C1})$ and vector B is defined by coordinates $(X_{C2}, Y_{C2})$. The category vectors can then be summed according to vector summation to produce the diagnostic vector. Notice that these two vectors are orthogonal to one another. According to vector summation, the magnitude of the vector is the square root of the sum of the squares, as follows:

Diagnostic Vector Magnitude $= \text{sqrt}(A^2 + B^2)$ $\text{sqrt}(X_{C1} * X_{C2} + Y_{C1} * Y_{C2})$ The angle of the diagnostic vector is calculated by the vector algebra dot product of vectors A and B, as follows:

$A \circ B = |A| * |B| \cos(\theta)$, where $\theta$ is the angle between A and B.

After the computations are made, the resulting diagnostic vector can be plotted on the Cartesian graph. FIG. 5 shows a diagnostic vector 502 that extends into zone 1. A quick review of the individual parameters reveals that they all represent healthy values, and hence the patient's overall cardiac health is satisfactory. In contrast, FIG. 6 shows a different diagnosis of cardiac health, where the patient appears to be deteriorating toward heart failure. In this case, the parameters all exhibit poor values in terms of cardiac health, causing the diagnostic vector 602 to extend into the red zone 2.

Figure 7:
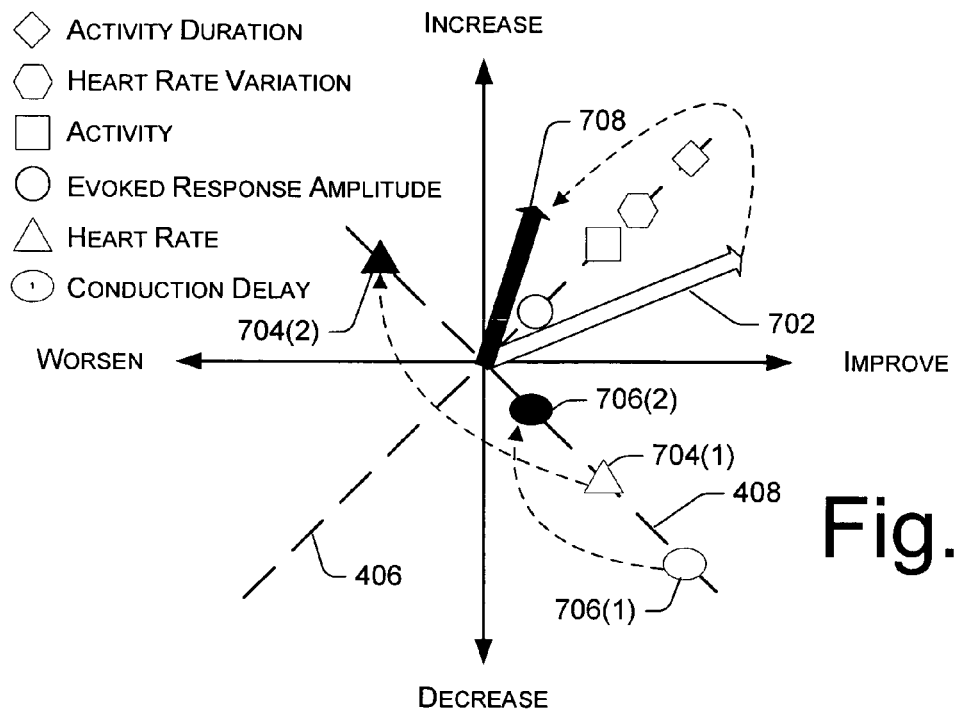

FIG. 7 shows a Cartesian graph 700 that illustrates how changes in diagnostic parameters measured over time by the implantable cardiac device results in movement and magnitude variations in the diagnostic vector. Such changes in the vector (both angle and magnitude) provide a progressive indicator of the patient's cardiac health, indicating whether the patient is improving or worsening. In this example, suppose an original diagnostic vector 702 is produced based on the six parameters: activity duration, heart rate variation, activity, evoked response amplitude, heart rate, and conduction delay.

Over time, certain parameters may change, for better or worse. In this example, measured parameters for heart rate and conduction delay degrade over time, as indicated by their northwesterly movement along the second diagonal 408 associated with the "decrease equals better" category. Specifically, heart rate changes from a first location 704(1) to a second location 704(2) on diagonal 408, and conduction delay migrates from a first location 706(1) to a second location 706(2) on the diagonal 408. The degradation may occur over a period of time, such as days, weeks, or months. A second diagnostic vector 708 is produced based on the original parameter values for activity duration, heart rate variation, activity, and evoked response amplitude and the two newer parameter values for heart rate and conduction delay.

As illustrated, as the parameters change, the diagnostic vector rotates counterclockwise and decreases in magnitude. The interpretation of this transition is that the patient's cardiac condition is worsening. Vector 702 suggests a fairly strong health situation, as the magnitude is comparatively large and the vector lies safely in the green zone 1. In contrast, vector 708 has less magnitude and extends into a yellow zone 3, suggesting a weakening cardiac condition.

Figure 8:
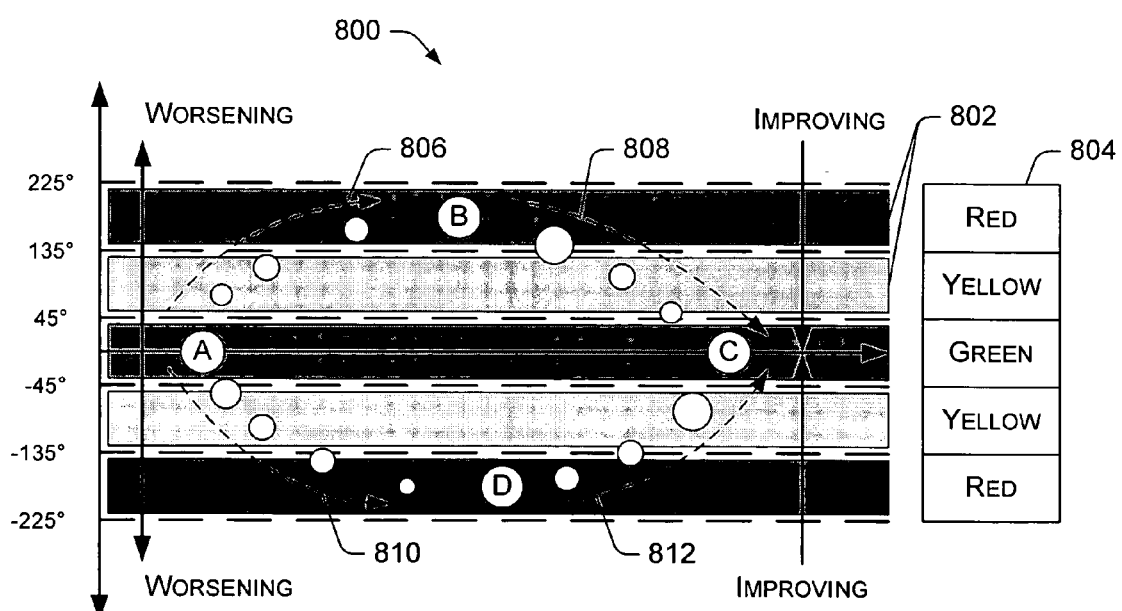
FIG. 8 illustrates one exemplary representation of a health trend graph that plots changes in the diagnostic vector over time to reveal changes in the patient's cardiac health.

FIG. 8 shows a health trend graph 800 that shows a patient's cardiac health over time. Time, vector angle, and vector magnitude are all represented on the trend graph 800. Each diagnostic vector derived from measured parameters during an evaluation period is represented by a symbol, which in this illustration is a circle. The size of each circle reflects the vector magnitude, with larger circles corresponding to larger magnitudes. Vector angle is measured along the y-axis and time is measured by the x-axis.

Horizontal bands 802 are drawn on the graph 800 to represent the 90° zones between the diagonals in the Cartesian graph 400 of FIG. 4. The middle band runs between −45° and +45°, corresponding to zone 1 in graph 400. Like zone 1, this band can be colored green, as shown in a color legend 804. The next two bands, between 45° and 135° and between −45° and −135°, correspond respectively to zones 3 and 4 in graph 400 and are colored yellow. The outer two bands, between 135° and 225° and between −135° and −225°, correspond to the same zone 2 of graph 400 and are colored red.

Movement of the vector around the Cartesian graph 400 in FIG. 4 is represented in the trend graph 800 by multiple instances of the circle. In this illustration, the circles follow four arc-shaped paths 806, 808, 810, and 812. The illustrated paths are merely examples of possible trends, and are provided for discussion purposes. Trends may exhibit any number of path shapes, and they need not be arc-shaped, smooth, or even resemble those shown in FIG. 8.

Path 806 shows a patient's cardiac condition worsening over time. Initially, the diagnostic vector represented by circle A has a relatively large magnitude (large circle) and an angle that places the vector in green zone 1 between the diagonals of −45° and +45°. Over time, the cardiac-related parameters collected by the implantable cardiac device begin to worsen, resulting in changes to the diagnostic vector. Specifically, the parameters classified along the "decrease equals better" diagonal 408 (e.g., heart rate and conduction delay) are getting worse, similar to the example of FIG. 7. This causes the vector magnitude to diminish as represented by smaller circles along path 806 and the vector angle to increase, thereby rotating the vector into the yellow zone 3 between the diagonals of +45° and +135°.

Eventually, most or all parameters begin to deteriorate, including those classified along the "increase equals better" diagonal 406 (e.g., activity duration, heart rate variation, activity, and evoked response amplitude). As those parameters slide along diagonal 406, onto the 225° line of the Cartesian graph, the vector direction moves into the red zone 2 between the diagonals of +135° and +225°, as represented by circle B in health trend graph 800. Also, in this red zone, the parameters are all relatively poor, thereby combining to produce a vector of larger magnitude in the red zone 1, as represented by the large circle B.

Path 808 shows another scenario where the patient is improving. The patient initially exhibits poor parameter values, as indicated by circle B in the red zone. Over time, the cardiac-related parameters collected by the implantable cardiac device begin to change for the better, resulting in changes to the diagnostic vector. The improving parameters cause the vector to more through the yellow zone back to the green zone, as represented by circle C.

Path 810 shows another scenario where the patient transitions from a healthy condition to an unhealthy condition. This scenario differs from the path 806 in that the parameters classified along the "increase equals better" diagonal 406 get worse before the other parameters classified along the "decrease equals better" diagonal 408. In this manner, the vector rotates from the green zone 1 through the yellow zone 4 between the diagonals of −45° and −135°. As most or all parameters begin to deteriorate, including those classified along the "decrease equals better" diagonal 408, the vector direction moves into the red zone 2 between the diagonals of −135° and −225° (which incidentally, is the same in the Cartesian graph as +135° and +225°) as represented by circle D in health trend graph 800.

Path 812 shows a fourth scenario in which the patient's cardiac health improves from poor health (circle D) to normal or good health (circle C).

User Interface

Figure 9:
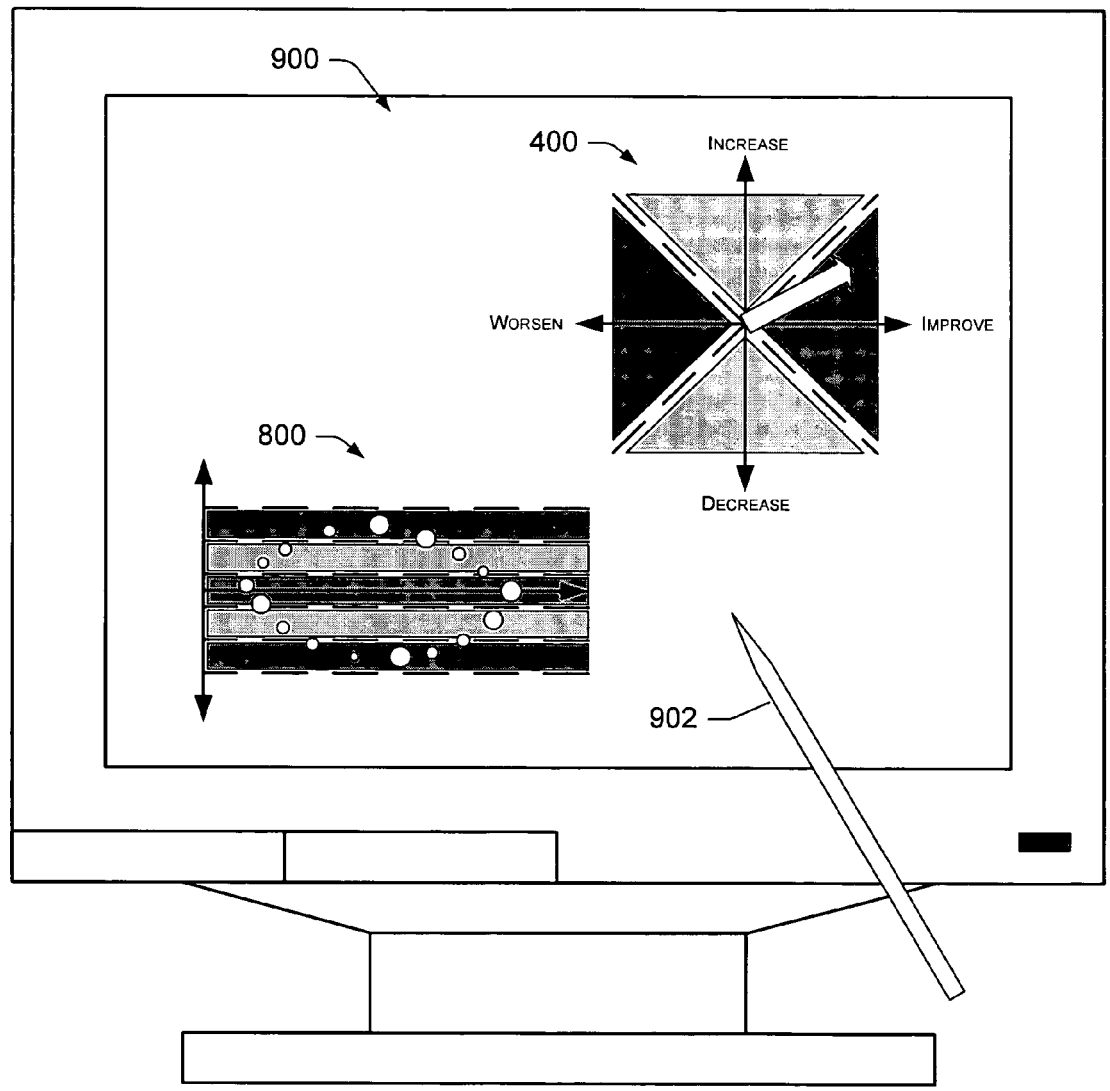
FIG. 9 illustrates a graphical user interface to enable user observation of, and interaction with, the diagnostic gauge of FIG. 4 and trend graph of FIG. 8.

The diagnostic graph 400 and health trend graph 800 may be presented to the physician, clinician, or other care provider as part of a graphical user interface. FIG. 9 shows one exemplary UI screen 900 that presents the diagnostic graph 400 and the health trend graph 800. Different or additional elements can be shown in other presentations (e.g., diagnostic statements, control buttons, etc.) and the elements may be arranged in other ways.

The diagnostic graph 400 provides a snap shot of the patient's general cardiac health for a given set of measurements. From this graph, the care provider can quickly ascertain whether the patient's general cardiac health is good, weak, or poor. The parameters measured by the implantable cardiac device are processed to form the diagnostic vector. Its magnitude and angle provide important information about the parameters. Larger magnitudes indicate that the parameters agree and the angle places the vector in different zones of the Cartesian graph, indicating whether most parameters are favorable, unfavorable, or a mix. The zones provide guidance as to which category of parameters may or may not be doing well.

The health trend graph 800 provides the care provider with a longer term view of the patient's cardiac health. From this graph, the care provider can discern whether the patient is improving or worsening over time. The time based paths 806, 808, 810, and 812 reveal patent's evolving cardiac health over many series of parameter measurements taken over a period of time (e.g., days, weeks, months).

A stylus 902 is provided to allow the clinician to interact with the user interface. As one possible example, the clinician might select the vector on graph 400 or a circle on graph 800 to reveal the underlying parameter values that combined to form the vector. Other forms of user input devices may also be used, such as a keyboard, mouse, or touch screen.

Operation

The implantable cardiac device 100 is implanted into a patient and over time begins to gather data that can be used as diagnostic parameters for the patient's cardiac health. The parameters are stored on the device 100 and processed by the parameter classification and analysis module 240 resident on the device. The parameters can be alternatively, or additionally, communicated from the device 100 to an external computing device (e.g., programmers 302, 308 and computing system 320) for processing by the parameter classification and analysis module resident on the external device.

Figure 10:
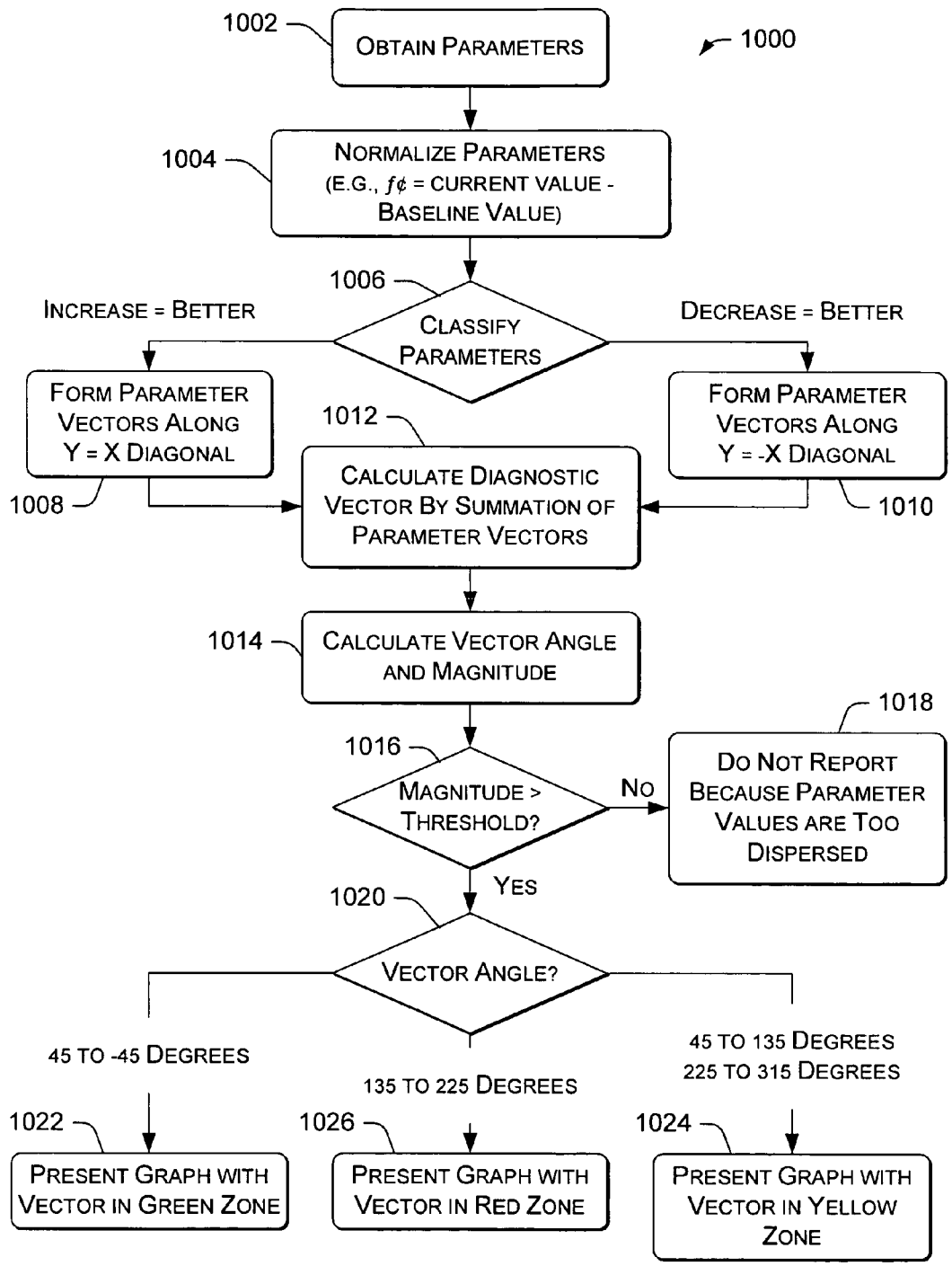
FIG. 10 is a flow diagram of an exemplary process for processing parameters measured by the implantable cardiac device to derive the diagnostic vector and present the diagnostic gauge.

FIG. 10 shows a process 1000 for processing parameters measured by the implantable cardiac device to derive a single diagnostic vector indicative of a patient's cardiac condition. In process 1000, operations are summarized in individual blocks. The operations may be performed in hardware and/or as machine-readable instructions (software or firmware) that can be executed by a processor, such as the microcontroller used in the implantable device or the processing units at programmers 302, 308 and computer system 320.

At block 1002, parameters are obtained for analysis. The parameters are related to cardiac health, with examples being activity duration, evoked response amplitude, activity, heart rate variation, heart rate, and conduction delay. Such parameters may be measured by the implantable cardiac device. Essentially any parameter that can be used in diagnosing heart failure may be used for analysis.

At block 1004, the parameters are normalized. As one technique, a delta is computed as the difference between the measured value and the baseline value. Suppose the activity value is 40, and the normal baseline is 30. The delta is +10. As another example, suppose the conduction delay is 100 ms and the normal baseline is 70 ms. The delta is 30 ms. Other normalization techniques may be used. Additionally, the parameters may be weighted based on the patient's prognosis.

At block 1006, the parameters are classified depending upon whether an increase in the measured value would be considered better health or worse health. Different linear functions are applied to the parameters depending upon the classification category, and these linear functions define vectors to be plotted in the Cartesian graph 400. If classified in the "increase equals better" category, the parameters are converted to vectors along the diagonal of the Cartesian graph defined by the linear function y=x (block 1008). Continuing our example involving an activity value with a delta of +10, the activity vector would extend from the origin to a point (+10, +10) given the function y=x. Conversely, if classified in the "decrease equals better" category, the parameters are converted to vectors along the diagonal of the Cartesian graph defined by the linear function y=−x (block 1010). Continuing our example involving the conduction delay with a delta of +30 ms, the conduction delay vector would extend from the origin to a point (+30, −30) given the function y=−x.

At block 1012, the individual parameter vectors for the various measured parameters are summed to produce a single diagnostic vector. At block 1014, the magnitude and angle of the resulting diagnostic vector are computed. One example of this calculation is described above.

At block 1016, it is determined whether the magnitude of the diagnostic vector exceeds a minimum threshold. The minimum threshold can be set by a care provider and is graphically illustrated as the circle about the origin in FIG. 4. If the vector does not exceed the threshold (i.e., the "No" branch from block 1016), the parameter values in this measured set are too dispersed and when summed, do not produce a vector of sufficient significance to give confidence to an interpretation (block 1018). Thus, the parameters are not reported and the diagnostic vector is not depicted on the diagnostic graph 400.

On the other hand, if the diagnostic vector exceeds the minimum threshold (i.e., the "Yes" branch from block 1016), the vector angle is examined to identify the appropriate zone of the diagnostic graph 400 (block 1020 in FIG. 10). If the angle is between +45° and −45°, the diagnostic graph 400 is presented with the diagnostic vector in green zone 1 (block 1022). If the angle is between +45° and +135° or between +225° and +315°, the diagnostic graph 400 is presented with the diagnostic vector in either yellow zone 3 or yellow zone 4, respectively (block 1024). If the angle is between +135° and +225°, the graph 400 is presented with the diagnostic vector in red zone 2 (block 1026).

Figure 11:
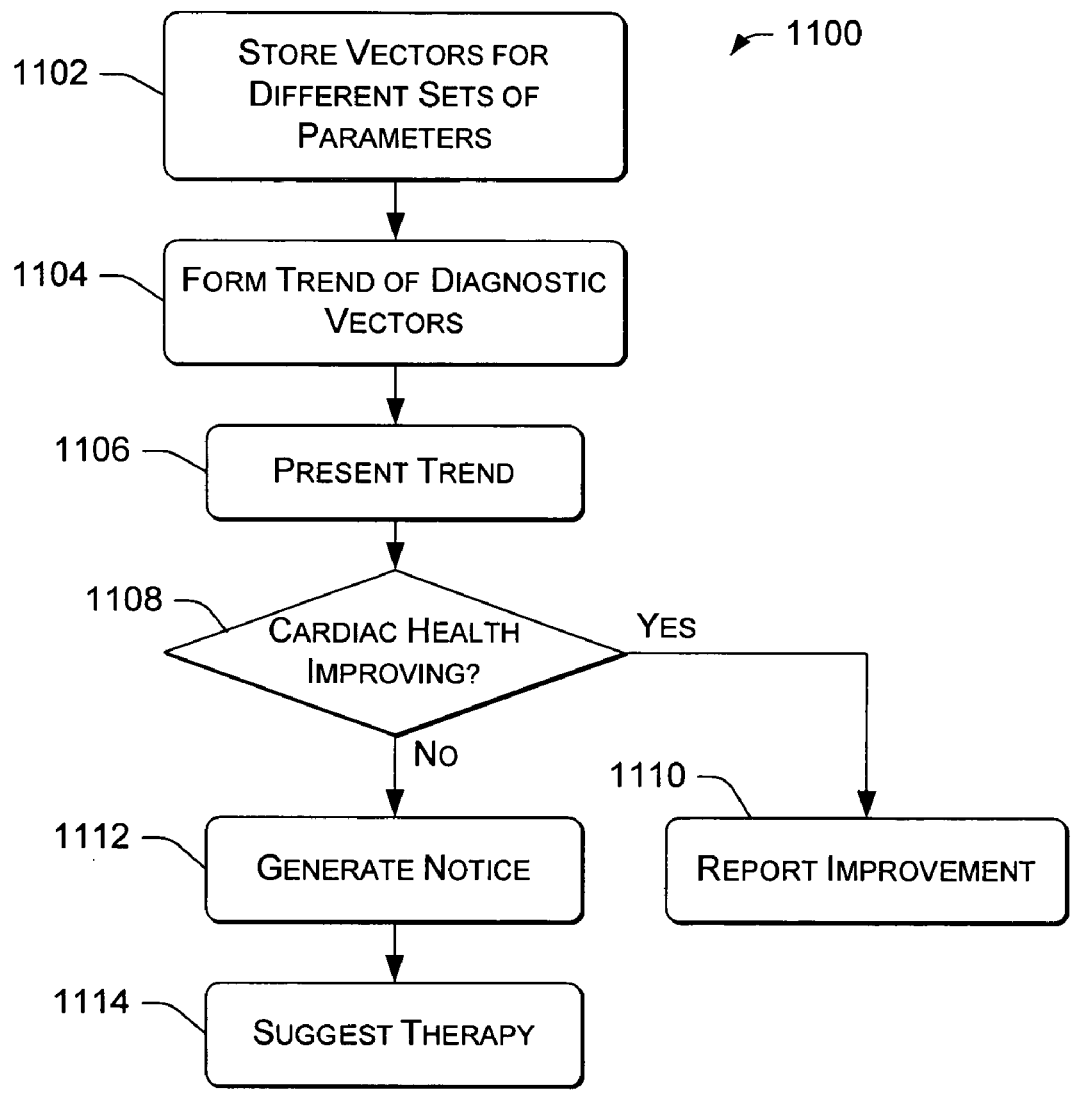
FIG. 11 is a flow diagram of an exemplary process for evaluating the patient's cardiac health over time.

FIG. 11 shows a process 1100 for evaluating a patient's health over time. At block 1102, diagnostic vectors derived for sets of parameter values collected over time (e.g., days, weeks, or months) are stored. The diagnostic vectors may be stored, for example, on the implantable device, the external programmer, the diagnostic computing system, and/or other locations.

At block 1104, a trend of the vectors is formed. The trend reveals changes in magnitude and angle in response to changes in underlying parameter values over time. At block 1106, the trend is presented to the care provider. One exemplary presentation form is the health trend graph 800 shown in FIGS. 8 and 9, where the vectors are plotted along a time axis and exhibit magnitude variations by enlarging or shrinking circles. Angle variations are manifest in paths through the colored bands. With this graph, the care provider can quickly ascertain whether the patient is improving or not.

If the patient's health is improving (i.e., the "Yes" branch from block 1108), the improving condition is reported to the care provider (block 1110). In addition to the graph 800, for example, the diagnostic computing system or programmer can display a message on the screen informing the care provider that the patient's health is improving.

If the patient's health is not improving (i.e., the "No" branch from block 1108), the trend graph 800 will show movement of the vector to the yellow and/or red bands and additionally, an alert can be generated (block 1112). The alert may be manifest in a variety of ways, including as a visual message depicted on a screen, or as a warning printed out on a recording medium, or as an audible alarm output by an external device.

At block 1114, a responsive therapy to combat the deteriorating condition may be optionally suggested. For instance, based on the worsening trend, a diagnostic program may be able to ascertain which parameters are causing the change and suggest a certain therapy that affects the parameters in a way to effectuate improvement in the patient's condition. As one example, if the conduction delay exceeds a threshold time delay, the therapy suggested may be to implement dual chamber pacing. As another example, if an implantable medication chamber is available, the therapy might be to release medication.

CONCLUSION

The foregoing discussion describes techniques for diagnosing a patient's health using fuzzy logic analysis. Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A method comprising:
   obtaining multiple parameters pertaining to a patient's cardiac health;
   computing a single diagnostic vector from at least four of the multiple parameters, the single diagnostic vector providing an assessment of the patient's cardiac health; and
   presenting the single diagnostic vector on a Cartesian graph having multiple zones, each zone having an associated diagnostic interpretation of a patient's cardiac health, wherein an angle of the single diagnostic vector places the single diagnostic vector in one of the zones to identify the associated diagnostic interpretation of the patient's cardiac health;
   wherein the computing a diagnostic vector comprises classifying the parameters into a first category where an increasing value equals an improving health condition and a second category where a decreasing value equals an improving health condition, wherein the Cartesian graph is defined by linear equation $y=x$ for the parameters of the first category, and wherein the Cartesian graph is defined by linear equation $y=-x$ for the parameters of the second category.

2. A method as recited in claim 1, wherein each of the parameters of the first category are normalized, weighted, and converted into first vectors, wherein each of the first vectors has an angle that aligns with a diagonal of the Cartesian graph defined by the linear equation $y=x$, wherein each of the parameters of the second category are normalized, weighted, and converted into second vectors, and wherein each of the second vectors has an angle that aligns with a diagonal of the Cartesian graph defined by the linear equation $y=-x$.

3. A method as recited in the claim 2, wherein the first vectors and the second vectors are summed to produced the single diagnostic vector, and wherein the single diagnostic vector is plotted on the Cartesian graph according to the magnitude and angle.

4. A method as recited in claim 1, wherein the Cartesian graph depicts a first diagonal line extending at 45 degrees and 225 degrees according to the linear equation $y=x$, a second diagonal line extending at 135 degrees and 315 degrees according to the equation $y=-x$, wherein the first and second diagonal lines define a first, second, third, and fourth zone, wherein the first zone is between 45 degrees and 315 degrees and spans positive x-axis and means that the patient exhibits satisfactory or good health, wherein the second zone is between 135 degrees and 225 degrees and spans a negative x-axis and means that the patient exhibits poor health conditions, wherein the third zone is between 45 degrees and 135 degrees along a positive y-axis and means that the patient is improving or worsening, and wherein the fourth zone is between 225 degrees and 315 degrees along the negative y-axis and means that the patient is improving or worsening.

5. A method as recited in claim 1, wherein the obtaining comprises measuring the parameters using an implantable device, wherein the parameters are selected from a group of parameters comprising arrhythmia, morphology-related data, impedance, evoked response amplitude, activity, activity variance, activity duration, posture, conduction delay, pressure, heart rate, heart rate recovery, heart rate variation, minute ventilation, and respiration.

6. A diagnostic system comprising:
   a memory to store multiple parameters related to a patient's cardiac health;
   a processing unit operative to compute a single diagnostic vector from at least four of the multiple parameters, wherein the single diagnostic vector comprises a magnitude and an angle that are used to interpret the patient's cardiac health; and
   a user interface to present the single diagnostic vector on a Cartesian graph to form a visual gauge that provides an assessment of the patient's cardiac health;
   wherein the Cartesian graph contains zones associated with degrees of wellness of the patient, wherein the angle places the single diagnostic vector in one of the zones to identify a diagnostic interpretation of the patient's cardiac health; and
   wherein the processing unit classifies the parameters into a first category where an increasing value equals an improving health condition and a second category where a decreasing value equals an improving health condition, wherein the Cartesian graph is defined by linear equation y=x for the parameters of the first category, and wherein the Cartesian graph is defined by linear equation y=−x for the parameters of the second category.

7. A diagnostic system as recited in claim 6, wherein each of the parameters of the first category are normalized, weighted, and converted into first vectors, wherein each of the first vectors has an angle that aligns with a diagonal of the Cartesian graph defined by the linear equation y=x, wherein each of the parameters of the second category are normalized, weighted, and converted into second vectors, and wherein each of the second vectors has an angle that aligns with a diagonal of the Cartesian graph defined by the linear equation y=−x.

8. A diagnostic system as recited in the claim 7, wherein the first vectors and the second vectors are summed to produced the single diagnostic vector, and wherein the single diagnostic vector is plotted on the Cartesian graph according to the magnitude and angle.

9. A diagnostic system as recited in claim 6, wherein the Cartesian graph depicts a first diagonal line extending at 45 degrees and 225 degrees according to the linear equation y=x, a second diagonal line extending at 135 degrees and 315 degrees according to the equation y=−x, wherein the first and second diagonal lines define the zones, wherein the zones comprise a first, second, third, and fourth zone, wherein the first zone is between 45 degrees and 315 degrees and spans a positive x-axis and means that the patient exhibits satisfactory or good health, wherein the second zone is between 135 degrees and 225 degrees and spans a negative x-axis and means that the patient exhibits poor health conditions, wherein the third zone is between 45 degrees and 135 degrees along a positive y-axis and means that the patient is improving or worsening, and wherein the fourth zone is between 225 degrees and 315 degrees along the negative y-axis and means that the patient is improving or worsening.

10. A diagnostic system as recited in claim 6, wherein the parameters are measured using an implantable medical device.

11. A system comprising:
an implantable device operative to sense multiple parameters;
an analysis system operative to construct a single diagnostic vector from at least four of the multiple parameters; and
a graphical user interface operative to present the single diagnostic vector as an assessment of a patient's health;
wherein the graphical user interface presents a Cartesian graph upon which the single diagnostic vector is plotted, the Cartesian graph having zones associated with degrees of wellness of the patient and the single diagnostic vector extends into one of the zones to indicate the patient's health; and
wherein the analysis system classifies the parameters into a first category where an increasing value equals an improving health condition and a second category where a decreasing value equals an improving health condition, wherein the Cartesian graph is defined by linear equation y=x for the parameters of the first category, and wherein the Cartesian graph is defined by linear equation y=−x for the parameters of the second category.

12. A system as recited in claim 11, wherein each of the parameters of the first category are normalized, weighted, and converted into first vectors, wherein each of the first vectors has an angle that aligns with a diagonal of the Cartesian graph defined by the linear equation y=x, wherein each of the parameters of the second category are normalized, weighted, and converted into second vectors, and wherein each of the second vectors has an angle that aligns with a diagonal of the Cartesian graph defined by the linear equation y=−x.

13. A system as recited in the claim 12, wherein the first vectors and the second vectors are summed to produced the single diagnostic vector, and wherein the single diagnostic vector is plotted on the Cartesian graph according to the magnitude and angle.

14. A system as recited in claim 11, wherein the Cartesian graph depicts a first diagonal line extending at 45 degrees and 225 degrees according to the linear equation y=x, a second diagonal line extending at 135 degrees and 315 degrees according to the equation y=−x, and wherein the first and second diagonal lines define the zones, wherein the zones comprise a first, second, third, and fourth zone, wherein the first zone is between 45 degrees and 315 degrees and spans positive x-axis and means that the patient exhibits satisfactory or good health, wherein the second zone is between 135 degrees and 225 degrees and spans a negative x-axis and means that the patient exhibits poor health conditions, wherein the third zone is between 45 degrees and 135 degrees along a positive y-axis and means that the patient is improving or worsening, and wherein the fourth zone is between 225 degrees and 315 degrees along the negative y-axis and means that the patient is improving or worsening.

15. A system as recited in claim 11, wherein the implantable device comprises an implantable cardiac device and the parameters are selected from a group of parameters comprising arrhythmia, morphology-related data, impedance, evoked response amplitude, activity, activity variance, activity duration, posture, conduction delay, pressure, heart rate, heart rate recovery, heart rate variation, minute ventilation, and respiration.

16. A system as recited in claim 11, wherein the analysis system computes individual vectors from the at least four parameters, and computes the single diagnostic vector from the individual vectors.

17. A system as recited in claim 11, wherein the zones of the Cartesian graph are color coded.

18. A system as recited in claim 11, wherein the analysis system is configured as part of the implantable device.

19. A system as recited in claim 11, wherein the analysis system is configured in a computing device separate from the implantable device.

* * * * *